United States Patent
Nord et al.

(10) Patent No.: US 10,328,279 B2
(45) Date of Patent: Jun. 25, 2019

(54) MEMORY AND APPARATUS PERTAINING TO THE AUTOMATED CALCULATION OF SUPPLEMENTAL PATIENT VOLUME INFORMATION

(71) Applicant: Varian Medical Systems International AG, Cham (CH)

(72) Inventors: Janne Nord, Espoo (FI); Juha Kauppinen, Espoo (FI); Jarkko Peltola, Tuusula (FI)

(73) Assignee: Varian Medical Systems International AG, Steinhausen (CH)

( * ) Notice: Subject to any disclaimer, the term of this patent is extended or adjusted under 35 U.S.C. 154(b) by 754 days.

(21) Appl. No.: 14/840,366

(22) Filed: Aug. 31, 2015

(65) Prior Publication Data
US 2017/0056687 A1 Mar. 2, 2017

(51) Int. Cl.
*A61N 5/10* (2006.01)
*G06F 19/00* (2018.01)

(52) U.S. Cl.
CPC ......... *A61N 5/103* (2013.01); *G06F 19/3456* (2013.01); *G06F 19/3481* (2013.01)

(58) Field of Classification Search
CPC .......... A61N 5/1049; A61N 2005/1074; A61N 5/103; A61N 5/1031; A61N 5/1039; A61N 2005/1061; A61N 5/1015; A61N 5/1038; A61N 5/1048; A61N 2005/1055; A61N 5/1067; A61N 5/1071; A61N 5/1081; A61N 5/1047; A61N 5/1065; G06F 19/3481; G06F 19/3456; G06T 2207/30004; G16H 50/20; G16H 50/30; G16H 10/60
See application file for complete search history.

(56) References Cited

U.S. PATENT DOCUMENTS

2017/0053562 A1 * 2/2017 Bova ...................... G09B 23/28

* cited by examiner

*Primary Examiner* — Maroun P Kanaan
(74) *Attorney, Agent, or Firm* — Fitch, Even, Tabin & Flannery LLP

(57) ABSTRACT

A control circuit that operably couples to a memory having a radiation-treatment plan stored therein that is based upon a particular patient volume receives subsequent information regarding that particular patient volume and automatically uses that subsequent information to calculate supplemental patient volume information to be used by the radiation-treatment plan. By one approach this supplemental patient volume information comprises replacement information to be used in lieu of the presumed patient volume information. The foregoing may include applying at least one rule to effect the aforementioned calculation, applying one or more deformable registration algorithms, and/or one or more Boolean operators.

14 Claims, 2 Drawing Sheets

MEMORY AND APPARATUS PERTAINING TO THE AUTOMATED CALCULATION OF SUPPLEMENTAL PATIENT VOLUME INFORMATION

TECHNICAL FIELD

This invention relates generally to radiation-treatment planning.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not discriminate between unwanted structures and adjacent tissues, organs, or the like that are desired or even critical to continued survival of the patient. As a result, radiation is ordinarily applied in a carefully administered manner to at least attempt to restrict the radiation to a given target volume.

Radiation-treatment plans typically serve to specify any number of operating parameters as pertain to the dynamic administration of such radiation dosings with respect to a given patient. For example, many treatment plans provide for exposing the target volume to possibly varying dosages of radiation from a number of different directions.

Such radiation-treatment plans typically presume any number of metrics regarding the target volume and/or other organs and tissues in the vicinity of the target volume. Examples of such metrics include, but are not limited to, such things as the size, shape, and orientation of external and/or internal portions of a given organ. These metrics are sometimes developed for a particular patient by referring to previously-obtained x-rays, computed tomography data, and so forth and other times by referring to historical data for other patients or as gleaned from atlases of such content.

Unfortunately, even the best radiation-treatment plan can be rendered less viable or even unusable when the patient's presumed physical circumstances change over time. As one simple example in these regards, a given patient's bladder may have a very different size from day to day (or during any given day) as a function of the volume of currently-retained urine. Many such variations are difficult or even impossible to predict.

BRIEF DESCRIPTION OF THE DRAWINGS

The above needs are at least partially met through provision of the memory and apparatus pertaining to the automated calculation of supplemental patient volume information described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit that operably couples to a memory having a radiation-treatment plan stored therein that is based upon a particular patient volume receives subsequent information regarding that particular patient volume and automatically uses that subsequent information to calculate supplemental patient volume information to be used by the radiation-treatment plan. By one approach this supplemental patient volume information comprises replacement information to be used in lieu of the presumed patient volume information.

By one approach, the control circuit applies at least one rule to effect the aforementioned calculation. By way of example this rule could comprise a rule regarding a location of a margin (such as an internal boundary) relative to a particular patient volume (such as a given organ). Such a rule, in turn, can facilitate calculating a specific volume while using that margin location.

These teachings are highly flexible in practice. For example, by one approach, the aforementioned use of the subsequent information to calculate the supplemental patient volume information can include calculating that supplemental patient volume information during a radiation-treatment session for the corresponding patient to thereby facilitate making real-time or near real-time changes in the radiation-treatment plan while also implementing that plan.

These teachings are also highly scalable in practice and will accommodate, for example, receiving a variety of different kinds of subsequent information for a given patient volume and/or receiving subsequent information for a variety of volumes in a given patient.

Figure 1:
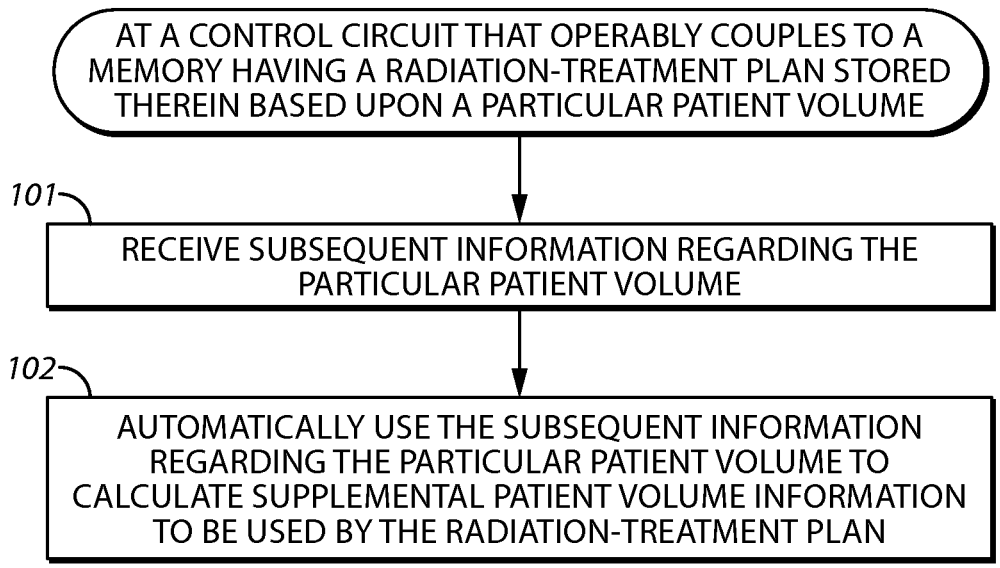
FIG. 1 comprises a flow diagram as configured in accordance with various embodiments of the invention.

These and other benefits may become clearer upon making a thorough review and study of the following detailed description. Referring now to the drawings, and in particular to FIG. 1, an illustrative process 100 that is compatible with many of these teachings will now be presented.

Figure 2:
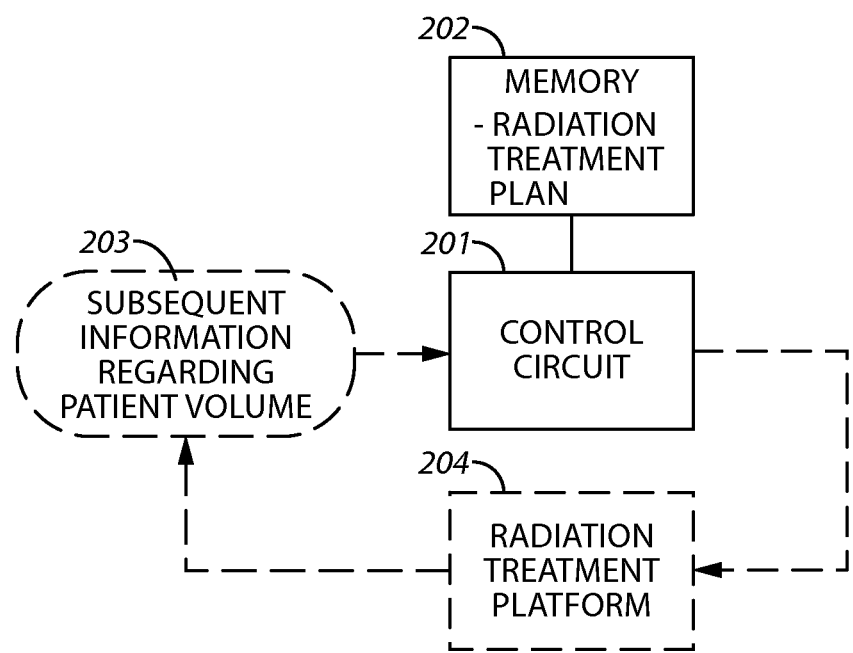
FIG. 2 comprises a block diagram as configured in accordance with various embodiments of the invention.

With reference as well to FIG. 2, for the purposes of this illustrative example it will be presumed that the control circuit 201 of a corresponding apparatus 200 carries out this process 100. This control circuit 201 operably couples to a memory 202 having at least one radiation-treatment plan stored therein as corresponds to a particular patient. More particularly, this radiation-treatment plan is based upon at least one particular patient volume. (In fact, many application settings will be concerned, one way or the other, with a plurality of separate patient volumes. For the sake of simplicity and clarity, however, this explanation will presume to use only a single particular patient volume.)

Generally speaking, a treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

The aforementioned particular patient volume can vary and the present teachings will accommodate a wide variety in this regard. By one approach, the particular patient volume can comprise the target volume; that is, the subject of the radiation treatment itself (such as, for example, a tumor). By another approach, the particular patient volume can comprise a non-targeted volume that is within the treatment volume and that is to be spared, to a greater or lesser extent, as much exposure to radiation as can reasonably be accommodated. In any event, the particular patient volume can comprise an entire organ or some portion thereof, tissue, or essentially any other biological structure as comprises a part of the patient.

The stored radiation-treatment plan can comprise a very recently completed plan (such as a plan that has been optimized within the context of a given radiation-treatment session) or a previously-completed plan (such as a plan that has been optimized hours, days, or even weeks prior to a given radiation-treatment session such as a present radiation-treatment session).

The radiation-treatment plan can be based upon the particular patient volume in a number of ways. By one approach, for example, the radiation-treatment plan can serve the explicit purpose of irradiating the particular patient volume or of specifically avoiding irradiating the particular patient volume (at all or to some specified degree or level). As another example, the location or position of all or part of the particular patient volume can in turn inform or otherwise impact decisions regarding when, how, and to what extent to conduct the administration of radiation as regards other patient volumes during the course of a treatment session.

By one approach this control circuit 201 serves to communicate a radiation-treatment plan to a corresponding radiation-treatment platform 204. These teachings will accommodate a wide variety of radiation-treatment platforms including, for example, so-called arc-therapy x-ray-based platforms. In some cases the control circuit 201 may in fact comprise a part of the radiation-treatment platform 204 while in other cases the control circuit 201 and the radiation-treatment platform 204 are separate physical and logical entities. These teachings will accommodate, for example, having the control circuit 201 co-located with the radiation-treatment platform 204 (for example, by having both housed within a shared facility such as a shared building) or having these two components remotely separated from one another by many miles.

Pursuant to this process 100, at step 101 the control circuit 201 receives subsequent information 203 regarding the aforementioned particular patient volume. As used herein, this reference to "subsequent" will be understood to refer a point in time that follows the availability of the aforementioned radiation-treatment plan. Accordingly, these teachings pertain to a situation where a radiation-treatment plan has been developed and optimized for a given patient, and then, prior to administering a corresponding radiation treatment to this patient, new information regarding this particular patient's volume of interest becomes available. By one approach, this subsequent information 203 regarding the particular patient volume becomes available during the corresponding radiation-treatment session itself and may even (though not necessarily) be developed and provided by the radiation-treatment platform 204.

Figure 3:
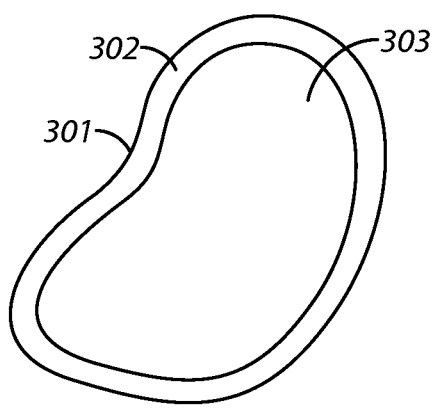
FIG. 3 comprises an illustrative image as configured in accordance with various embodiments of the invention.

As a simple, illustrative example in these regards, the stored radiation-treatment plan may have presumed a particular shape, size, and orientation for a given organ 301 (in this case, a bladder) as shown in FIG. 3. The information available in these regards may include a particular patient volume that comprises the wall 302 of the organ 301 that surrounds an inner space 303 (that may be filled, for example, with unexpelled urine). The presumed specifics for this organ 301 may be based, for example, upon previous information obtained for this patient in a previous treatment or diagnostic session or may have been gleaned, for example, from an available atlas.

Figure 4:
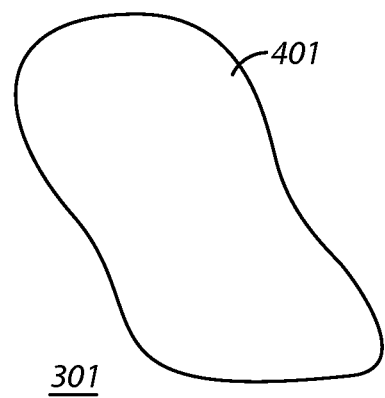
FIG. 4 comprises an illustrative image as configured in accordance with various embodiments of the invention.

To continue with this example, however, the subsequent information 203 regarding this particular organ 301 (as gleaned, for example, via application of an appropriate contouring algorithm in combination with new imaging data) as shown in FIG. 4 reflects a different shape 401 and/or orientation. Such changes may be somewhat rare or at least modest with some patient volumes. With many patient volumes, however, changes with respect to size, shape, and/or orientation are to be expected over time. An organ such as the bladder is a useful example in these regards as at least the size of the organ will of course vary over time with the amount of contained urine.

To the extent that the radiation-treatment plan in this example is based upon the bladder's wall 302, the shift in position as exemplified in FIGS. 4 and 3 represents a potentially significant change that can impact the intended and expected efficacy of the radiation-treatment plan. These concerns can include reducing the therapeutic results as regards the targeted volume and/or increasing the risk of unwanted collateral harm to non-targeted structures.

At step 102 of this process 100, the control circuit 201 automatically uses this subsequent information 203 regarding the particular patient volume to calculate supplemental patient volume information to be used by the radiation-treatment plan. By one approach, for example, the calculated supplemental patient volume information can be replacement patient volume information that the radiation-treatment plan uses in substitution for the previous information regarding the particular patient volume.

Figure 5:
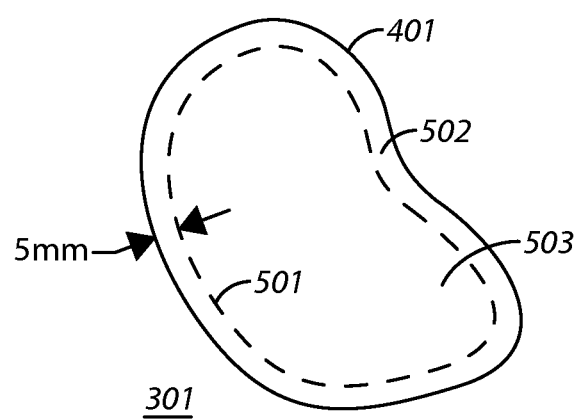
FIG. 5 comprises an illustrative image as configured in accordance with various embodiments of the invention.

The present teachings will accommodate a variety of approaches as regarding the calculation of the supplemental patient volume information. By one approach, for example, the control circuit 201 can calculate the supplemental patient volume information by automatically applying at least one rule. By way of example, such a rule can comprise, for example, a rule regarding a location of a margin relative to the particular patient volume. Referring to FIG. 5, and by way of further example, this approach could comprise calculating an inner periphery 501 by applying a rule that this inner periphery 501 is 5 millimeters inward of the outer boundary of this particular organ 301. The control circuit 201 can then use this presumed/calculated location of the inner margin to make corresponding calculations regarding, for example, the wall volume 502 for this organ 301 and/or the interior 503 of the organ 301 (in absolute terms and/or in relation to other orientation or relative points of reference as desired).

Such rules can be as varied and as empirical or deterministic as may be desired. There are, in fact, many already-existing rules of this sort available in the known art (though such rules have not been automatically applied as described herein).

That said, however, the present teachings will accommodate other approaches with respect to calculating the supplemental patient volume information (either in lieu of a rule-based approach or in combination therewith). As one approach in these regards, this calculation can comprise automatically otherwise determining a difference between the particular patient volume and the subsequent information regarding that particular patient volume. Such a calculation can comprise using, for example, one or more deformable registration algorithms as are well understood in this art.

As another non-limiting illustrative example in these regards, this calculation can comprise using one or more Boolean operation to calculate the supplemental patient volume information. Useful Boolean operations can include, but are not limited to, Boolean intersections and subtractive operations. For example, a radiation-treatment plan for treating a lung tumor will typically attempt to dose lung tissue that surrounds the target (tumor) volume as little as possible. An automatically-delineated "lung," however, typically represents the whole lung volume, including the target volume and the surrounding lung tissue. A Boolean operation can serve to subtract the target volume from the "lung" volume. Dosimetric analysis of a candidate treatment plan can then be carried out using these two non-overlapping volumes (i.e., the lung volume without the target volume and the target volume).

As another example in these regards, when evaluating the dose delivered to healthy tissue within a certain distance D from a target volume, a representative margin volume can be generated. This operation can comprise calculating a volume that is an enlarged copy of the target volume by using the distance D and then subtracting the target volume from the enlarged volume to yield a peripheral volume. This peripheral volume excludes the target volume but contains the healthy tissue around the target volume within the distance D from the target volume.

The present teachings are highly flexible in practice and will further accommodate, for example, calculating the supplemental patient volume information to be used by the radiation-treatment plan, at least in part, as a function of machine geometry as pertains to the radiation-treatment platform 204 that effects the radiation-treatment plan. As one simple example, this could comprise employing different rules depending upon a particular angle of the radiation source with respect to the patient during the course of a radiation-treatment session. This could comprise, for example, using a first rule regarding a given margin within a first range of treatment fields and a second, different rule regarding that same margin within a second, different range of treatment fields (to accommodate the observation, for example, that the wall thickness of a given organ varies with respect to the viewing angle).

The control circuit 201 referred to herein can comprise a fixed-purpose hard-wired platform or can comprise a partially or wholly programmable platform as desired. These architectural options are well known and understood in the art and require no further description here. This control circuit 201 is configured (for example, by using corresponding programming as will be well understood by those skilled in the art) to carry out one or more of the steps, actions, and/or functions described herein.

The aforementioned memory 202, in turn, may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

In addition to storing the aforementioned radiation-treatment plan this memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

So configured, such a control circuit 201 can readily adapt to changes (including either or both or near-term changes as well as real-time changes, as desired) as occur with respect to a patient's geometry. These teachings are readily scaled to accommodate a wide variety of slowly or rapidly changing structures (including, for example, a patient's lungs).

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. An apparatus comprising:
   a radiation-treatment platform;
   a memory having a radiation-treatment plan stored therein to be carried out by the radiation-treatment platform, the radiation-treatment plan based upon a particular patient volume;
   a control circuit operably coupled to the memory and to the radiation-treatment platform and being configured to:
   receive subsequent information from the radiation-treatment platform regarding the particular patient volume;
   automatically use the subsequent information regarding the particular patient volume to calculate supplemental patient volume information to be used by the radiation-treatment plan by, at least in part, automatically applying at least one rule regarding a location of a margin relative to the particular patient volume wherein the margin is calculated as an inner periphery located a specific distance inwardly of an outer boundary of the particular patient volume;
   automatically use the supplemental patient volume information with the radiation-treatment plan to adapt to changes with respect to a patient's geometry.

2. The apparatus of claim 1 wherein the subsequent information regarding the particular patient volume comprises information received during a radiation-treatment session and the control circuit is configured to use the subsequent information to calculate the supplemental patient volume information during the radiation-treatment session.

3. The apparatus of claim 1 wherein the subsequent information regarding the particular patient volume comprises a volume calculated, at least in part, using the location of the margin.

4. The apparatus of claim 1 wherein the control circuit is configured to automatically use the subsequent information regarding the particular patient volume to calculate the supplemental patient volume information by automatically determining a difference between the particular patient volume and the subsequent information regarding the particular patient volume.

5. The apparatus of claim 4 wherein the control circuit is configured to automatically determine the difference between the particular patient volume and the subsequent information regarding the particular patient volume by using a deformable registration algorithm.

6. The apparatus of claim 1 wherein the control circuit is configured to automatically use the subsequent information regarding the particular patient volume to calculate the supplemental patient volume information by automatically using at least one Boolean operation to calculate the supplemental patient volume information.

7. The apparatus of claim 1 wherein the control circuit is configured to automatically use the subsequent information regarding the particular patient volume to calculate the supplemental patient volume information to be used by the radiation-treatment plan as a function, at least in part, of machine geometry as pertains to a radiation-treatment apparatus that effects the radiation-treatment plan.

8. A method comprising:
at a control circuit that operably couples to a radiation-treatment platform and to a memory having a radiation-treatment plan stored therein to be carried out by the radiation-treatment platform, the radiation-treatment plan based upon a particular patient volume;
receiving subsequent information from the radiation-treatment platform regarding the particular patient volume;
automatically using the subsequent information regarding the particular patient volume to calculate supplemental patient volume information to be used by the radiation-treatment plan by, at least in part, automatically applying at least one rule regarding a location of a margin relative to the particular patient volume wherein the margin is calculated as an inner periphery located a specific distance inwardly of an outer boundary of the particular patient volume;
automatically using the supplemental patient volume information with the radiation-treatment plan to adapt to changes with respect to a patient's geometry.

9. The method of claim 8 wherein the subsequent information regarding the particular patient volume comprises information received during a radiation-treatment session and automatically using the subsequent information regarding the particular patient volume to calculate supplemental patient volume information to be used by the radiation-treatment plan comprises automatically using the subsequent information regarding the particular patient volume to calculate the supplemental patient volume information during the radiation-treatment session.

10. The method of claim 8 wherein the subsequent information regarding the particular patient volume comprises a volume calculated, at least in part, using the location of the margin.

11. The method of claim 8 wherein automatically using the subsequent information regarding the particular patient volume to calculate the supplemental patient volume information comprises automatically determining a difference between the particular patient volume and the subsequent information regarding the particular patient volume.

12. The method of claim 11 wherein automatically determining the difference between the particular patient volume and the subsequent information regarding the particular patient volume comprises using a deformable registration algorithm.

13. The method of claim 8 wherein automatically using the subsequent information regarding the particular patient volume to calculate the supplemental patient volume information comprises automatically using at least one Boolean operation to calculate the supplemental patient volume information.

14. The method of claim 8 wherein automatically using the subsequent information regarding the particular patient volume to calculate the supplemental patient volume information to be used by the radiation-treatment plan comprises automatically using the subsequent information regarding the particular patient volume to calculate the supplemental patient volume information to be used by the radiation-treatment plan as a function, at least in part, of machine geometry as pertains to a radiation-treatment method that effects the radiation-treatment plan.

* * * * *